United States Patent
Wong et al.

(10) Patent No.: US 10,500,018 B2
(45) Date of Patent: Dec. 10, 2019

(54) MULTI-FUNCTIONAL DENTAL TOOL

(71) Applicant: Julielynn Yee-Ching Wong, Toronto (CA)

(72) Inventors: Julielynn Yee-Ching Wong, Toronto (CA); Anush Sushant Agarwal, Brampton (CA); Gerald Joseph Ennett, Goderich (CA); Sachin Hiral Paresh Doshi, Toronto (CA)

(73) Assignee: Julielynn Yee-Ching Wong, Toronto (CA)

( * ) Notice: Subject to any disclaimer, the term of this patent is extended or adjusted under 35 U.S.C. 154(b) by 0 days.

(21) Appl. No.: 15/671,784

(22) Filed: Aug. 8, 2017

(65) Prior Publication Data

US 2018/0042697 A1    Feb. 15, 2018

Related U.S. Application Data

(60) Provisional application No. 62/372,446, filed on Aug. 9, 2016.

(51) Int. Cl.
| | |
|---|---|
| *A61C 3/10* | (2006.01) |
| *A61C 1/08* | (2006.01) |
| *A61C 3/06* | (2006.01) |
| *A61C 3/08* | (2006.01) |

(52) U.S. Cl.
CPC ............... *A61C 3/10* (2013.01); *A61C 1/088* (2013.01); *A61C 3/06* (2013.01); *A61C 3/08* (2013.01)

(58) Field of Classification Search
CPC .. A61C 3/10; A61C 1/088; A61C 3/06; A61C 3/08; A61C 3/14; A61C 3/16; A45D 26/00; A45D 26/0066
See application file for complete search history.

(56) References Cited

U.S. PATENT DOCUMENTS

| | | | |
|---|---|---|---|
| 2,497,418 A | 2/1950 | Schroeder | |
| 2,696,048 A * | 12/1954 | Lindgren | A61C 3/08 433/162 |
| 3,769,663 A * | 11/1973 | Perl | G02C 11/04 224/181 |
| 4,917,517 A | 4/1990 | Ertz | |
| 5,180,239 A | 1/1993 | Bistrack | |
| 5,334,215 A * | 8/1994 | Chen | A61B 17/30 294/99.2 |
| 6,988,814 B1 * | 1/2006 | Correa | A61B 17/30 362/109 |
| 2008/0217507 A1 | 9/2008 | McKenzie | |
| 2015/0147712 A1 * | 5/2015 | Cannon | A61C 19/004 433/29 |

\* cited by examiner

*Primary Examiner* — Heidi M Eide
(74) *Attorney, Agent, or Firm* — Blake, Cassels & Graydon LLP; Brett J. Slaney

(57) ABSTRACT

A multi-functional dental tool is provided to be used for the dental filling of teeth after the removal of damage in the teeth. The dental tool includes a forcep portion on one end and a burnisher tool on the other end. The burnisher tool portion includes a flat burnisher and a ball burnisher, and a joint which connects the forcep portion and the burnisher tool portion. The dental tool can also include a penlight holder which can receive and secure a penlight. The penlight, when secured in the penlight holder, provides illumination when performing the filling procedure, especially in situations in which an overhead light source is not readily available.

13 Claims, 11 Drawing Sheets

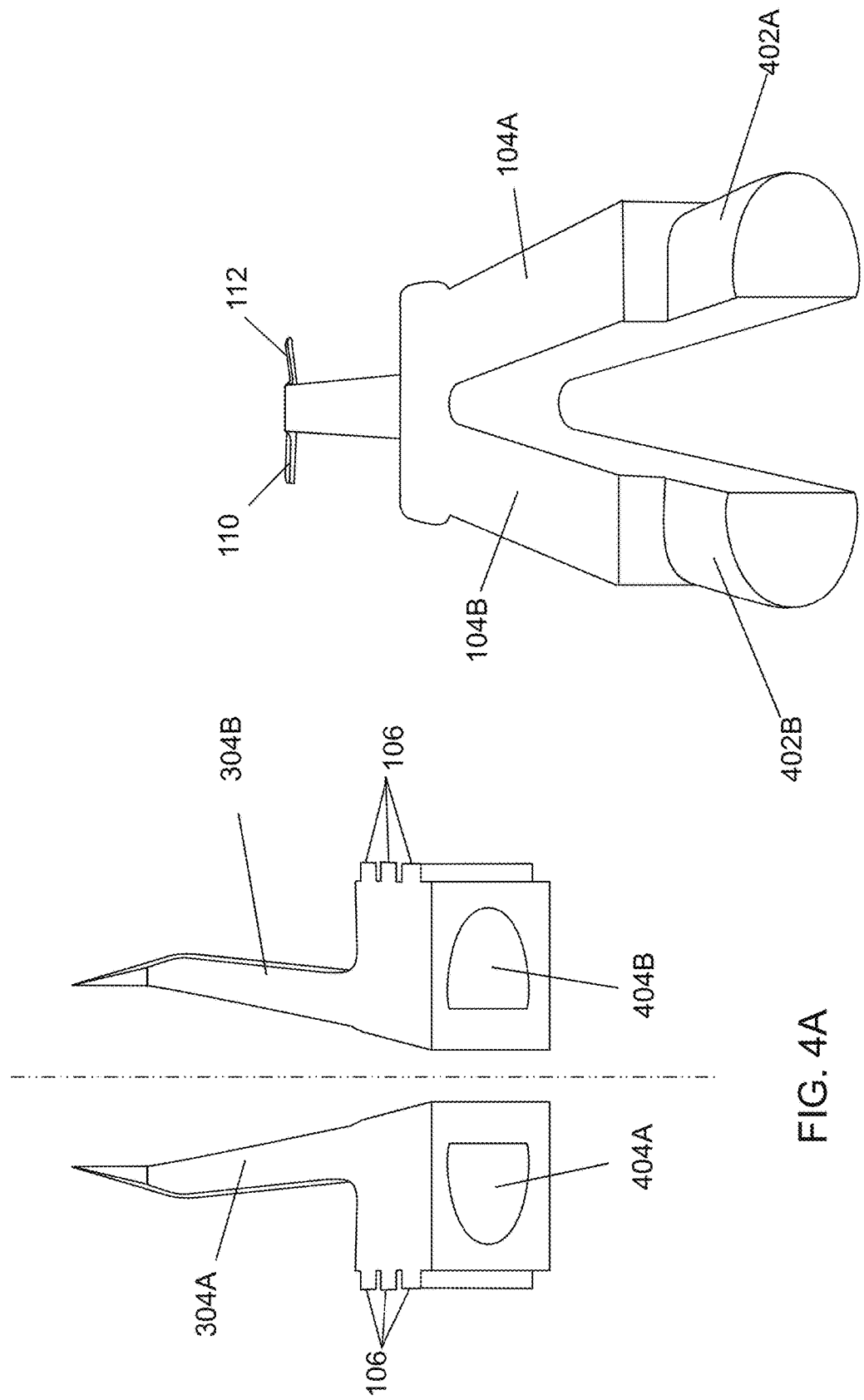

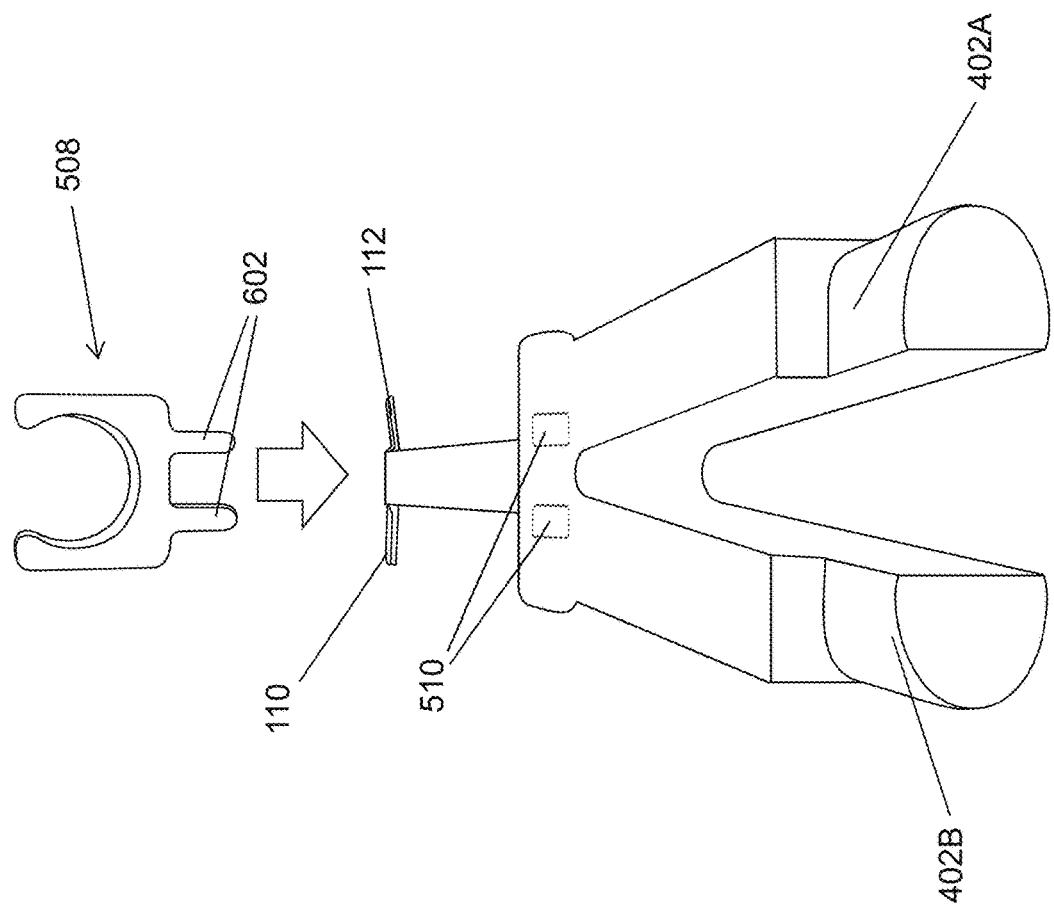

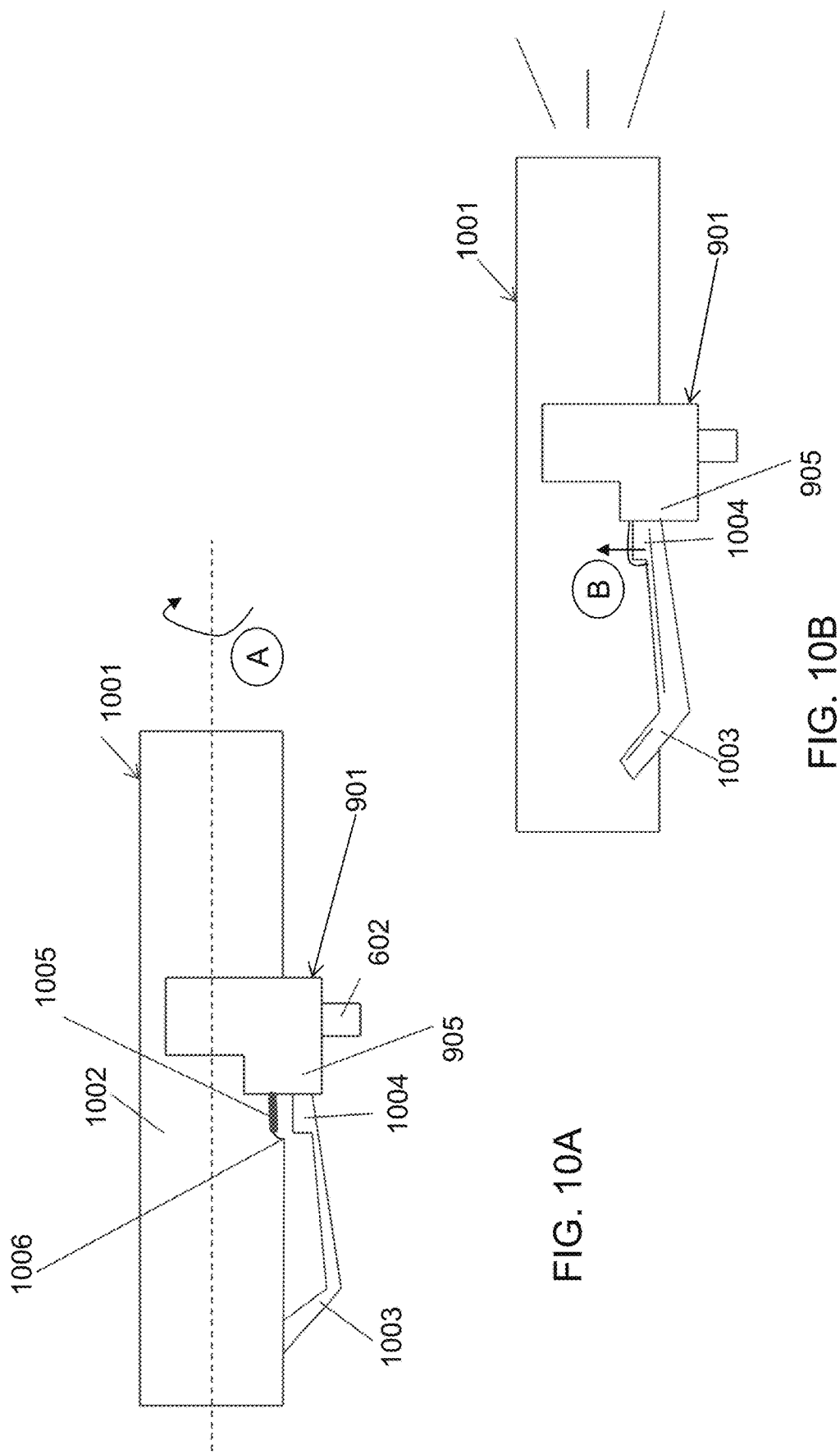

MULTI-FUNCTIONAL DENTAL TOOL

CROSS-REFERENCE TO RELATED APPLICATION

The present application claims priority to U.S. Patent Application No. 62/372,446 filed on Aug. 9, 2016, and titled "Multi-Functional Dental Tool", the entire contents of which are herein incorporated by reference.

TECHNICAL FIELD

The following relates to a dental tool which may be used during a dental filling procedure.

DESCRIPTION OF THE RELATED ART

Teeth are a set of bone-like calcified tissue that are used to mechanically break down items of food by crushing them in preparation for swallowing and digestion. Teeth, like all parts of the body, are prone to damage and wear as they are used daily. Sometimes, a tooth will develop damage in the form of erosion of the enamel, the outer coating of the tooth, cavities, or other types of decay. Often times, the damaged parts of an affected tooth will be removed and a filling procedure will be performed, which substitutes a filling material in the removed areas so that the shape and function of the tooth can be substantially restored.

The filling procedure begins with the removal of the damaged areas of an affected tooth. This is usually done with a dental drill. Then, the individual performing the filling, such as, but not necessarily, a dentist, cleans the affected area of the tooth of interest using a gauze or some other cleaning material. The gauze is held by forceps. Then the individual puts permanent filling material, which is commonly made of gold, porcelain, silver amalgam, or a composite resin, or temporary filling material, on to a burnishing tool and transfers this material to the affected area. Finally, the filling material is spread and molded to the shape of the original tooth with a separate burnishing tool, and also polished to ensure that the filling material hardens. The filling material used for the procedure depends on factors such as the location of the affected tooth, severity of the damage, and wishes of the patient. For example, for a front tooth, a composite resin filling that matches the tooth in color may be used, whereas for a back molar tooth, the more durable silver amalgam filling may be used. To perform the filling procedure, a forcep, gauze and a plurality of different burnishers are commonly used.

BRIEF DESCRIPTION OF THE DRAWINGS

Embodiments will now be described by way of example only with reference to the appended drawings wherein:

FIG. 4A shows a detailed view of the removable forcep end portions shown in FIG. 3.

FIG. 4B shows the dental tool excluding the removable forcep portions.

FIG. 7 shows an example embodiment of how the removable penlight from FIG. 5B may attach to the dental tool of FIG. 5B.

FIGS. 10A and 10B show a penlight rotated within the penlight holder shown in FIG. 9, in order to turn on or turn off the penlight.

DETAILED DESCRIPTION

Figure 1:
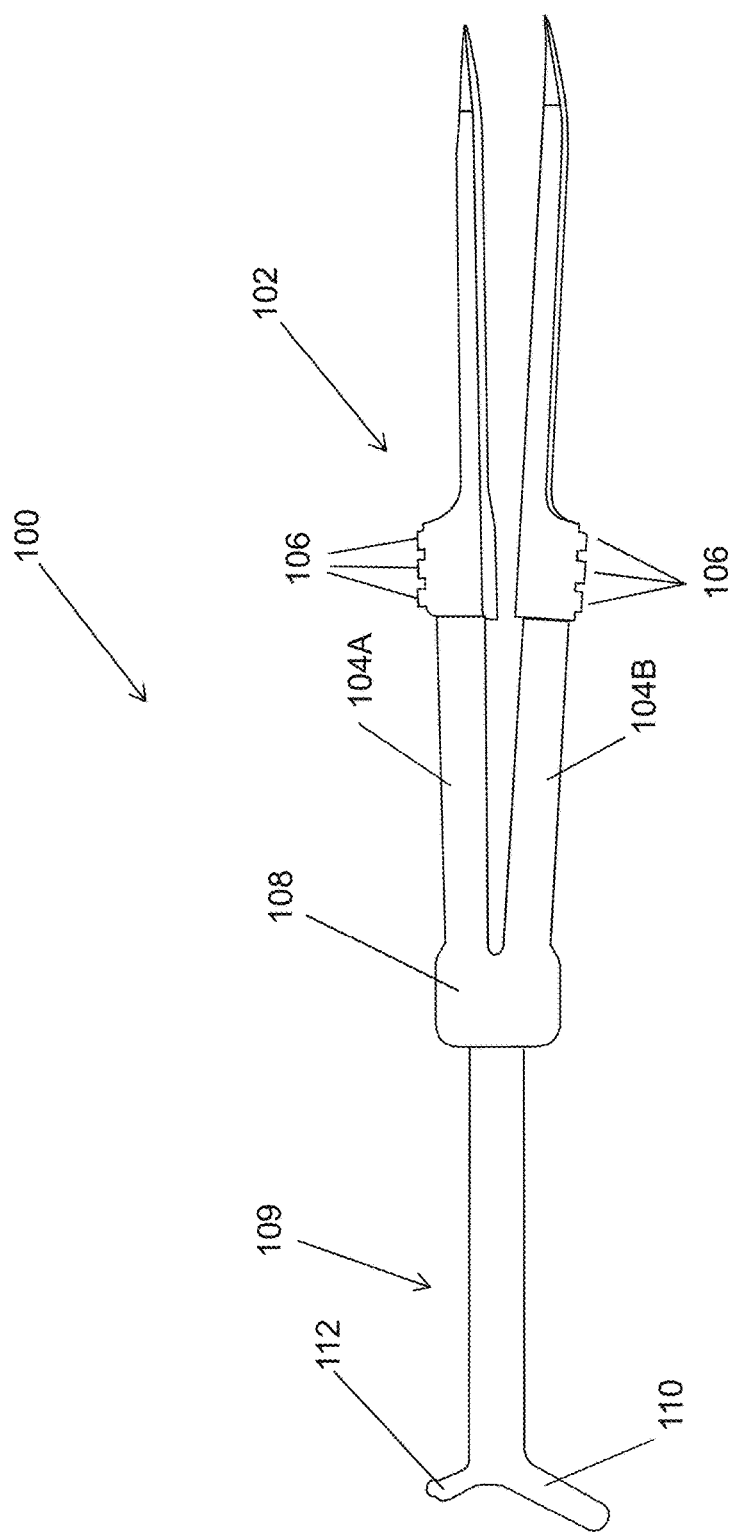
FIG. 1 is a top side view of the dental tool, according to an example embodiment.

It will be appreciated that for simplicity and clarity of illustration, in some cases, reference numerals may be repeated among the figures to indicate corresponding or analogous elements. In addition, some details or features are set forth to provide a thorough understanding of the embodiments described herein. However, it will be understood by those of ordinary skill in the art that the embodiments described herein are illustrative examples that may be practiced without these details or features. In other instances, well-known methods, procedures and components have not been described in detail so as not to obscure the invention illustrated in the examples described herein. Also, the description is not to be considered as limiting the scope of the example embodiments described herein or illustrated in the drawings.

A tooth filling procedure provides a way to restore a tooth that has been damaged by decay back to its normal function and shape. After the decay has been removed from the affected tooth, filling the tooth involves a generally quick and painless procedure of cleaning the tooth of interest, filling the space originally taken by the damaged portion with a filling material, and carefully molding and polishing the filling material to ensure that the tooth of interest can return to its normal function and shape. By closing off spaces where bacteria can enter, a filling helps prevent further decay from occurring in the affected tooth.

In many scenarios in which an individual's tooth has developed cavities or some other type of damage which can be treated with a simple dental filling procedure, or in which a pre-existing filling has gotten loose or fallen out, it is unfortunately the case that that individual cannot receive it. One reason for this is that there is no proper dental clinic that is accessible, for example, if the individual resides in a region of a country in which dental clinics are sparse (e.g. in developing countries or rural areas). Another reason for improper or no dental treatment is that there may not be a readily available overhead light source, which is used to illuminate inside an individual's mouth. Yet another reason may be that the individual is somewhere outside the reach of aid where the proper tools and materials needed to treat the individual may not be present, such as in space (e.g. a space craft, a space station, etc.). In fact, dental filling replacements must at times be performed in space by crew medical officers. This may occur, for example, because when astronauts move large objects in microgravity, the inertia of mass and velocity can potentially cause facial injuries, teeth damage, and thereby, filling loss. As well, astronauts could experience dislocation, clenching, grinding, or chewing which could cause a pre-existing filling to loosen and fall out. Although medical tools may be brought onboard the space station, all of the needed tools may not always be taken or readily found. For a temporary replacement dental filling, the following instruments and materials are typically used: a forcep, a flat burnisher, a ball burnisher, a gauze or other cleaning material, and temporary filling material. In a space mission in which one objective is to lighten the weight within the spacecraft, especially during take-off, some of the aforementioned materials may be left behind, lost in-transit or unintentionally forgotten. Similar difficulties arise for military hospitals, disaster relief operations, visiting doctors, and isolated habitats (e.g. at sea, underwater, in the Arctic, in the Antarctic, etc.).

Although a dental filling procedure is relatively quick and simple with the right tools and materials, the consequences of not receiving it, or even delaying it for too long, can have extreme and costly consequences. If a cavity or damage in a patient's tooth is not treated properly or overlooked for long enough, it can lead to the painful deterioration of the tooth, making it necessary for the patient to go through a root canal procedure or even extraction of the tooth.

It is herein recognized that there are multiple challenges in performing a dental filling procedure in certain settings due to location and material constraints. The multi-functional dental tool described herein addresses one or more the aforementioned problems associated with receiving a dental filling in a timely manner.

Figure 2:
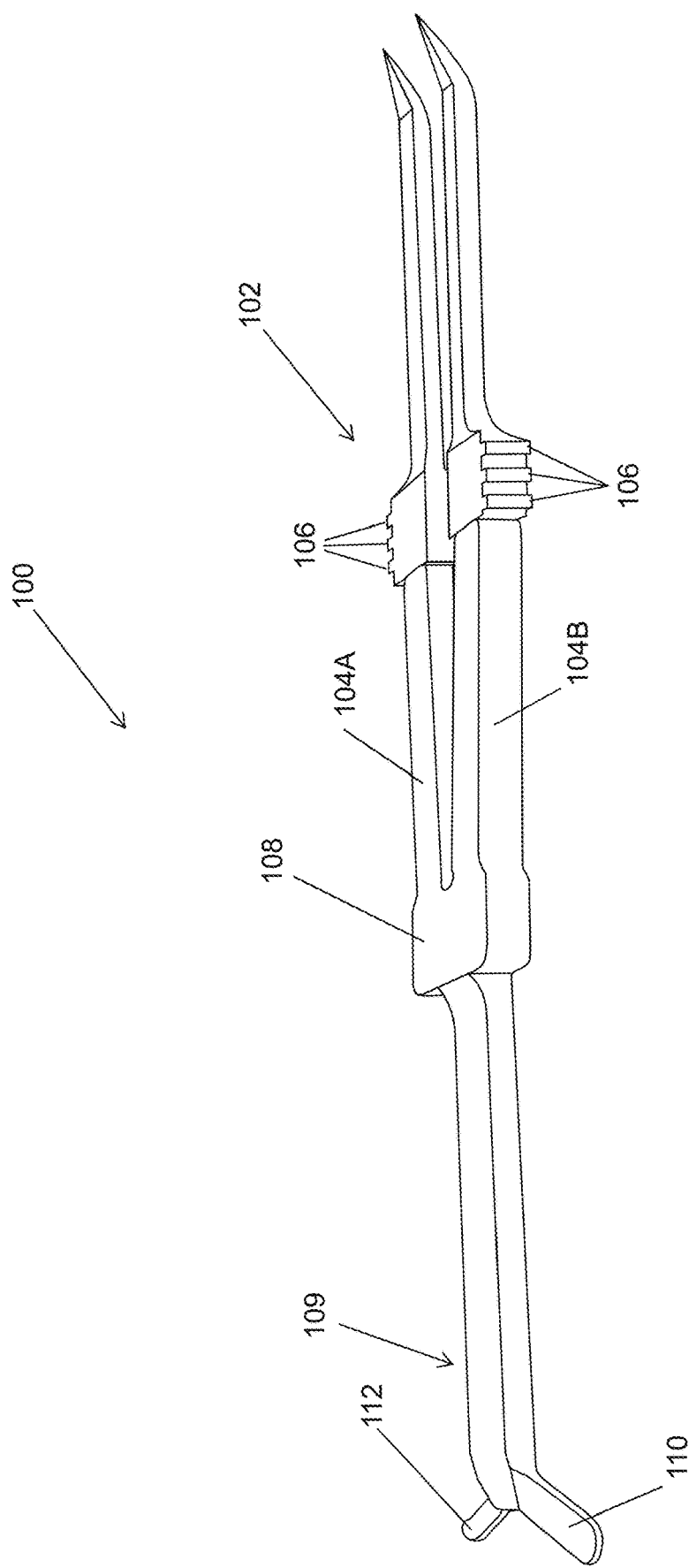
FIG. 2 is a perspective view of the dental tool of FIG. 1.

FIG. 1 is a top down view of a multi-functional dental tool 100, also herein called "dental tool", according to an example embodiment. FIG. 2 is a perspective view of the dental tool in FIG. 1. On the one end of the dental tool, there is provided a forcep 102 with forcep legs 104A and 104B, each with a set of grips 106 which may aid the user when gripping the forcep 102. The grips, for example, are formed by a grooves in a surface. In other words, the grips 106 are designed for better grip by the user's fingers. Other types of gripping configurations or surfaces may be used to improve grip.

When the forcep legs 104A and 104B are pressed towards each other, they are brought together such that forcep tips 107 touch each other. On the other end of the dental tool 100, there is provided a dental burnishing tool 109 with two different burnishing ends 110, 112 arranged in a Y-configuration or a T-configuration.

For example, there is one flat burnisher 110 (also called a paddle) and one ball burnisher 112. The flat burnisher 110 has a substantially flat surface, a rectangular cross-section and a rounded rectangular edge, while the ball burnisher 112 has a substantially flat surface and a substantially round edge. The flat burnisher 110 is longer in length than the ball burnisher 112. The burnishing tool 109 and the forcep 102 meet at a joint 108 which connects the two tools. In this way, the example embodiment in FIGS. 1 and 2 combines the features of a forcep, a flat burnisher, and a ball burnisher, three of the main tools needed for a dental filling, into one portable and lightweight tool.

In another example embodiment, the two burning ends include any combination of: an amalgam plugger, a condenser, a serrated condenser, a smooth condenser, an interproximal condenser, a football burnisher, an acorn burnisher, a paddle, a beaver tail burnisher, a ball burnisher, a carver, a hollenback carver, a dycal/liner applicator, an excavator, a hatchet, and an explorer. In another example, the two ends are variants of the same instance of the tool (e.g. a larger paddle and a smaller paddle).

In yet another example embodiment, there is only a single burnishing end on the burnishing tool 109, rather than two burnishing ends as shown in the figures.

The dental tool 100 may be made of a durable material such as steel, tungsten carbide, titanium nitride, plastic, or a combination thereof, depending on the how the dental tool 100 may be used. For example, if a resin composite filling material will be used, a titanium nitride instrument may be better suited as it has a low-stick property when in contact with a composite filling material, allowing the material to be better spread and molded around the affected tooth. To take another example, if the goal is to have a lightweight tool, a main ingredient for the dental tool 100 may be a plastic material. The dental tool 100 may be made using traditional fabrication methods, or 3D printing methods, or both.

After the damaged part(s) of a tooth has been removed from an affected tooth, an example process of filling a patient's tooth goes as follows. The individual performing the filling uses the forcep portion 102 of the dental tool 100 to pick up a portion of gauze or other cleaning material between the forcep tips 107 while using the grips 106 for additional gripping support. The gauze is used to clean the tooth of interest. The individual performing the filling then uses the flat burnisher 110 to scoop up the filling material such as an amalgam, a composite resin, or porcelain, and then transports the filling material to the tooth of interest. The filling material is applied to the tooth. The individual then uses the ball burnisher 112 to mold and polish the filling material to resemble the shape of the original tooth and also to polish, or burnish, the material so that it can harden and become durable.

Figure 3:
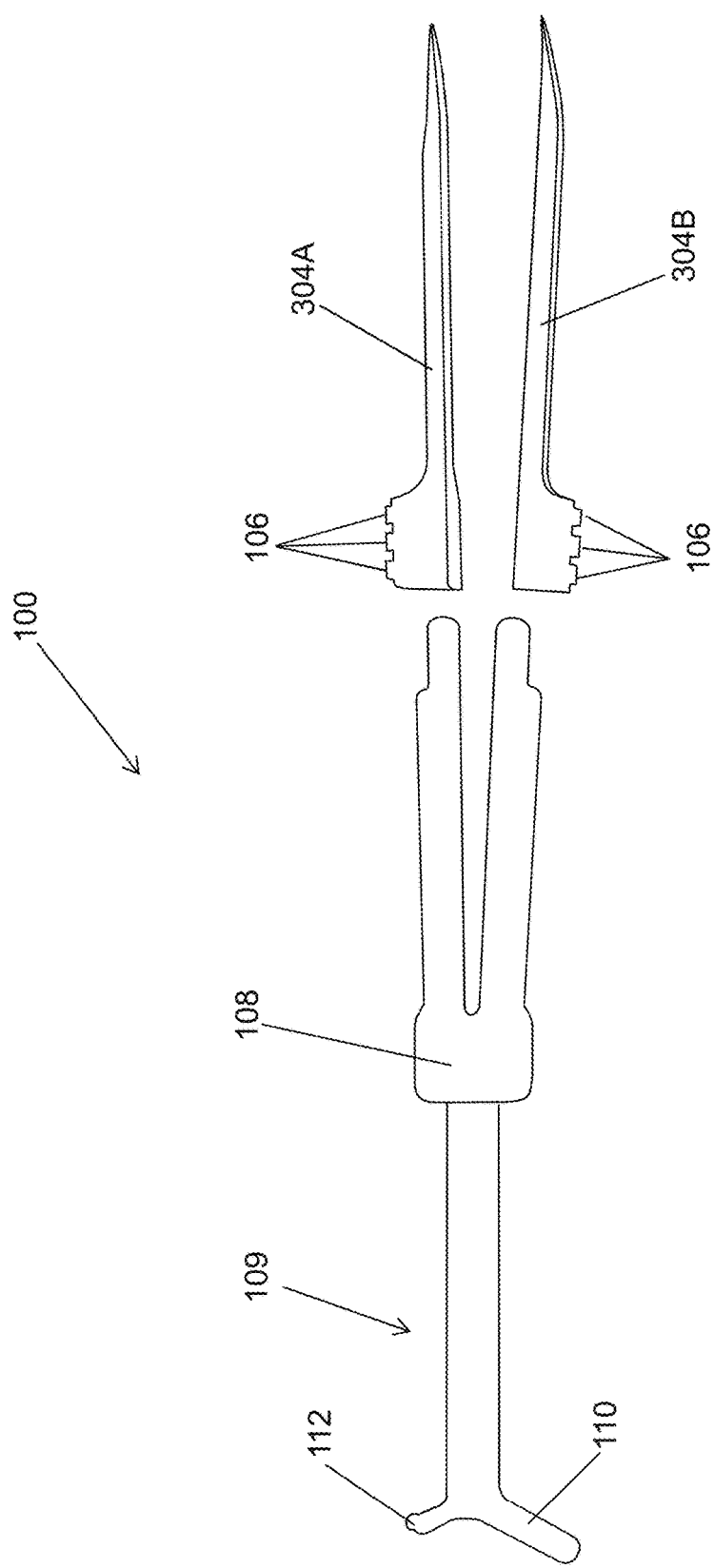
FIG. 3 is a top view of the dental tool for which the end portions of the forcep are removable, according to an example embodiment.

FIG. 3 shows an alternative example embodiment in which the dental tool 100 is not one unitary piece, but rather a kit of parts. In this embodiment, each forcep leg 104A and 104B has an end portion 304A and 304B that is removable from the rest of the dental tool 100. This ability of the dental tool 100 to disassociate into a kit of parts may help the dental tool 100 be more portable by allowing the pieces to be packed in a more compact manner. In an example embodiment, the end portion 304A, 304B may be sterilized separately and different (e.g. cleaner) forcep end portions may be interchanged with the body with the joint 108 between uses.

In another example embodiment, for the purposes of manufacturing by 3D printing, there may be some advantages in fabricating the separate parts as shown in FIG. 3.

FIGS. 4A and 4B show in detail how the removable pieces may fit together to become one whole dental tool. FIG. 4B shows a detailed view of the dental tool 100 without the removable forcep end portions 304A and 304B. At the part where the removable forcep portions 304A and 304B may be attached to the dental tool 100, there are two inserts 402A and 402B. Each insert 402A and 402B fits into a corresponding hole located on each removable forcep portion 304A and 304B to secure the removable forcep portions 304A and 304B to the rest of the forcep legs 104A and 104B.

FIG. 4A shows a detailed view of the removable forcep portions 304A and 304B in isolation. The removable forcep portions 304A and 304B, respectively, have holes or cavities 404A, 404B defined therein that are shaped to receive the inserts 402A, 402B. When attaching the removable forcep portions 304A and 304B, the holes 404A and 404B may allow the two inserts 402A and 402B, respectively, to be pushed into them, so that that the removable forcep portions 304A and 304B are locked into place. The assembled dental tool resembles the unitary dental tool shown in FIGS. 1 and 2, and is used in the same way.

As shown by FIGS. 4A and 4B, the holes 404A and 404B in the removable forcep portions 304A and 304B are shaped in such a way that they may allow the inserts 402A and 402B to fit into them when they are positioned in a certain orientation. For example, the orientation in which the removable forcep portions 304A and 304B, when secured to the rest of the forcep legs 104A and 104B, ensure that the grips 106 face outwards towards the hand of the user, to aid the user in gripping the forcep 102 properly. In the example, the grips face outward when the dental tool is assembled. Thus, when the removable forcep portions 304A and 304B are secured onto the rest of the dental tool 100, they are positioned to be mirror images of each other. Since they are mirror images of each other, the removable forcep portion 304A, once flipped about the axis shown in dotted lines in FIG. 4A, can be fitted with the insert 402B. Similarly, the removable forcep portion 304B, once flipped about the axis shown in dotted lines in FIG. 4A, can be fitted with the insert 404A. In an embodiment in which the forcep portions 304A and 304B have been attached to forcep legs 104B and 104A, respectively, it follows that the when the dental tool 100 is laid on its bottom side, the pointed ends of the forcep 102 point downwards rather than upwards.

In an example embodiment, the holes 404A, 404B and the inserts 402A, 402B are shaped similar to half-moons. However, other shapes that facilitate similar principles as noted above are also applicable.

In another example embodiment, other attachment mechanisms between the removable forcep portions and the forcep legs may be used. For example, clips, snaps, magnetic material and other retention mechanisms may be used. In another example, the inserts are on the removable forcep portions and the corresponding holes are defined within the forcep legs.

Figure 5B:
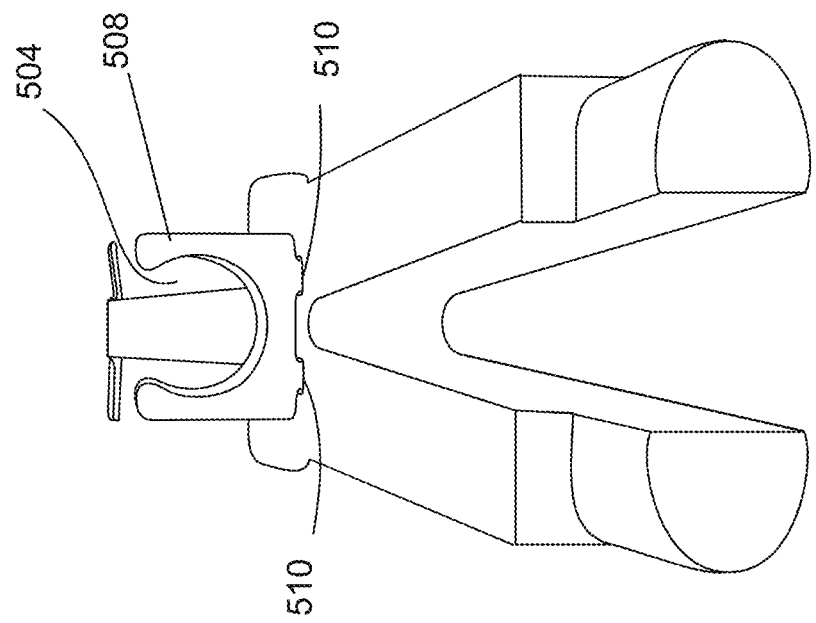
FIG. 5B shows another example embodiment of the dental tool which has a removable penlight holder that is able to attach onto, and detach from, the dental tool.
Figure 5A:
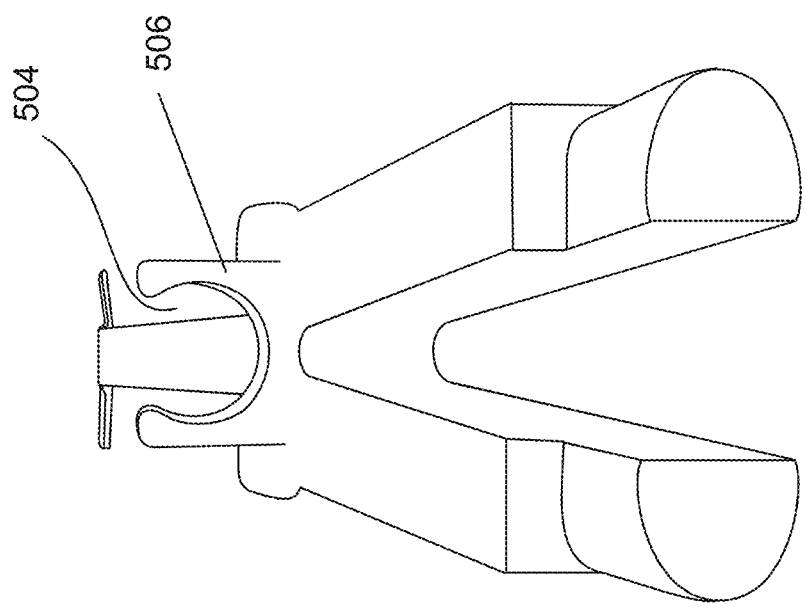
FIG. 5A shows an example embodiment of the dental tool which has a penlight holder positioned at the joint of the dental tool.

FIG. 5A shows another example embodiment of the dental tool 100, in which there is provided a penlight holder 506 that is shaped like a U-shaped bracket. The penlight holder is positioned at the joint 108 between the forcep portion 102 and the burnisher tool portion 109, and receives and secures a penlight in the circular space 504 defined by the penlight holder 506. The penlight holder is positioned at the joint 108 because it allows the penlight, when attached to the dental tool 100 via the penlight holder 506, to rest comfortably in the nook that is formed in the user's hand when gripping the dental tool 100. In FIG. 5A, the penlight holder 506 is not removable from the dental tool 100. In another example, the penlight holder and the entire dental tool, including the forcep legs, are a unitary body.

Alternatively, FIG. 5B shows an example embodiment in which there is a removable penlight holder 508 which can be detached and reattached to the dental tool 100. In this embodiment, the dental tool 100 defines a pair of holes 510 and the penlight holder has a set of corresponding prongs, which may fit into the two holes 510 so that the penlight holder 508 can be secured onto the dental tool 100. It will be appreciated that other attaching mechanisms (e.g. an "attacher") for reasonably securing the penlight holder 508 to the joint portion 108 are applicable. In both embodiments of FIGS. 5A and 5B, the forcep portions 304A and 304B (not shown) may be removable as implied by these particular embodiments, or they may also be permanently attached to the dental tool 100 as in FIG. 1. In both embodiments of FIGS. 5A and 5B, a penlight can be secured the dental tool 100 in two orientations: one in which the light, when the penlight is turned on, shines in the direction of the forcep 102, and another in which the light, when the penlight is turned on, shines in the direction of the burnisher tool 109.

In this way, the penlight can be used to provide extra visibility inside of a patient's mouth during different stages of the filling process, especially in settings in which an overhead light source is not readily available.

It will be appreciated that there may be different sizes of the penlight holder, so as to accommodate different diameters of penlights. These different sizes of penlight holders may be manufactured using conventional manufacturing methods, or by 3D printing. For example, the penlight holder can be easily customized with 3D printing to fit a specific penlight diameter.

Figure 6A:
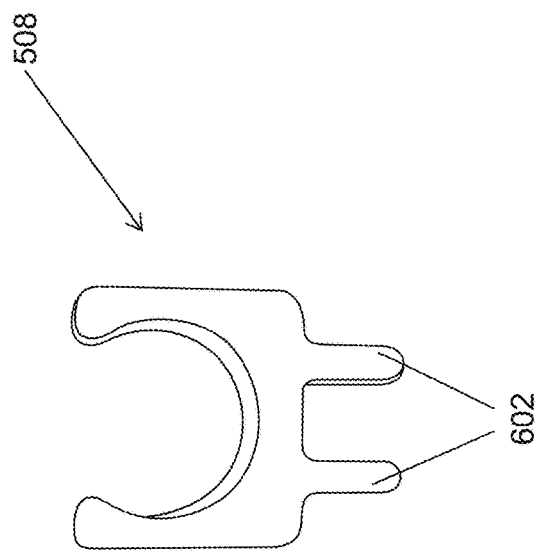
FIG. 6A shows a detailed view of the removable penlight holder shown in FIG. 5B, but in isolation.

FIG. 6A shows a detailed view of the removable penlight holder 508 shown in FIG. 5B. When the set of prongs 602 are inserted into the holes 510, the penlight holder 508 can be secured onto the joint 108 of the dental tool 100. The cross section of the prongs 602, and therefore the shape of the holes 510, may be of a rounded rectangle geometry, as shown in the embodiments. They may also be of a different shape, as long as the prongs 502 correspond to the shape of the holes 510 so that the prongs 602 can fit into the holes 510.

Figure 6B:
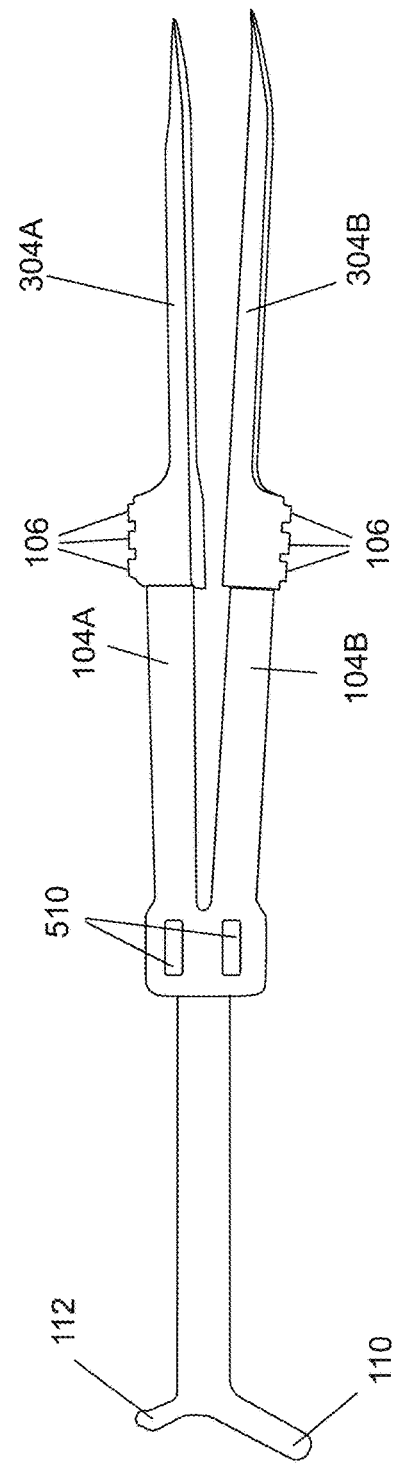
FIG. 6B shows the dental tool shown in FIG. 5B excluding the removable penlight holder.

FIG. 6B shows the dental tool 100 with the pair of holes 510 through which the prongs 602 fit. In this embodiment. Similar to FIGS. 5A and 5B, the forcep portions 304A and 304B may be removable or they may also be permanently attached to the dental tool 100 as in FIG. 1.

In an example embodiment, other attachment mechanisms for the penlight holder may be used in alternative to prongs and holes, including, magnets, clips, snaps, Velcro, a friction-fit mechanism, or combinations thereof.

FIG. 7 demonstrates an example embodiment how the removable penlight holder 508 may attach to the dental tool 100. Since the penlight holder 508 is removable, it can be inserted from the top as shown in this figure, or from the bottom. Being able to attach the penlight holder 508 to the dental tool 100 on the top or the bottom may be useful as the user inspects different parts of the mouth. For example, the tooth of interest may be a top molar tooth, in which case it may be advantageous to attach the penlight holder 508, and therefore the penlight, on the top side. If, however, the tooth of interest is a bottom tooth, it may be advantageous to attach the penlight holder 508, and therefore the penlight, on the bottom side for better visibility of the tooth of interest. Similar to FIGS. 5A and 5B, the forcep portions 304A and 304B (not shown) may be removable as implied by this particular embodiment, or they may also be permanently attached to the dental tool 100 as in FIG. 1.

Figure 8A:
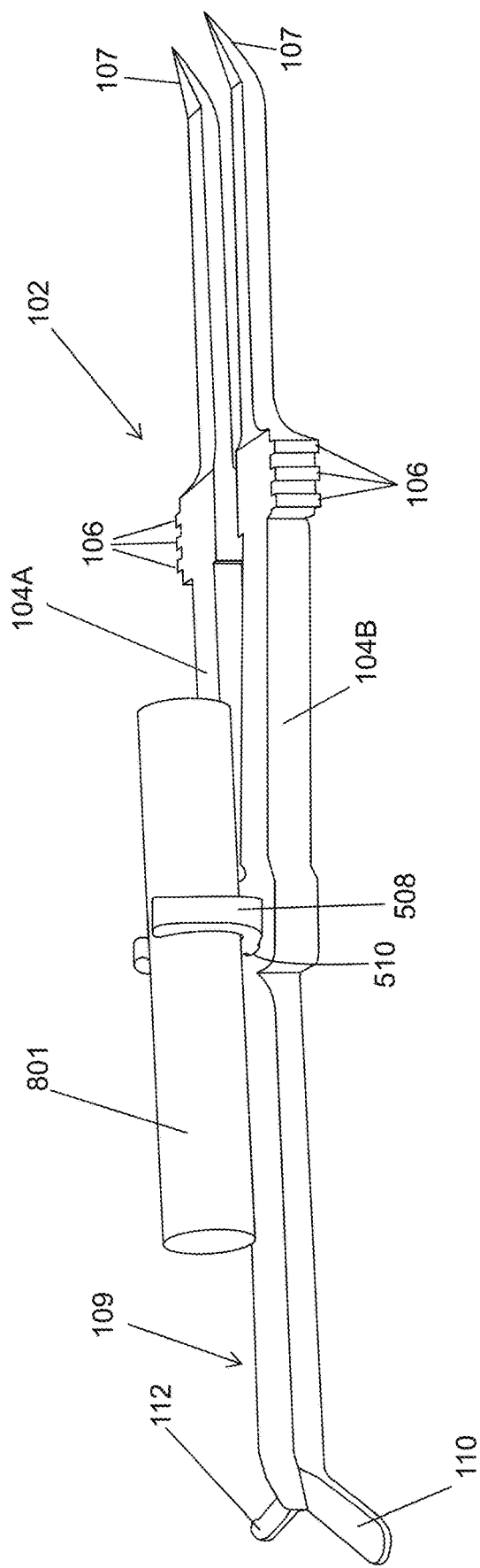
FIGS. 8A and 8B show a full dental tool with a removable penlight holder in different positions.
Figure 8B:
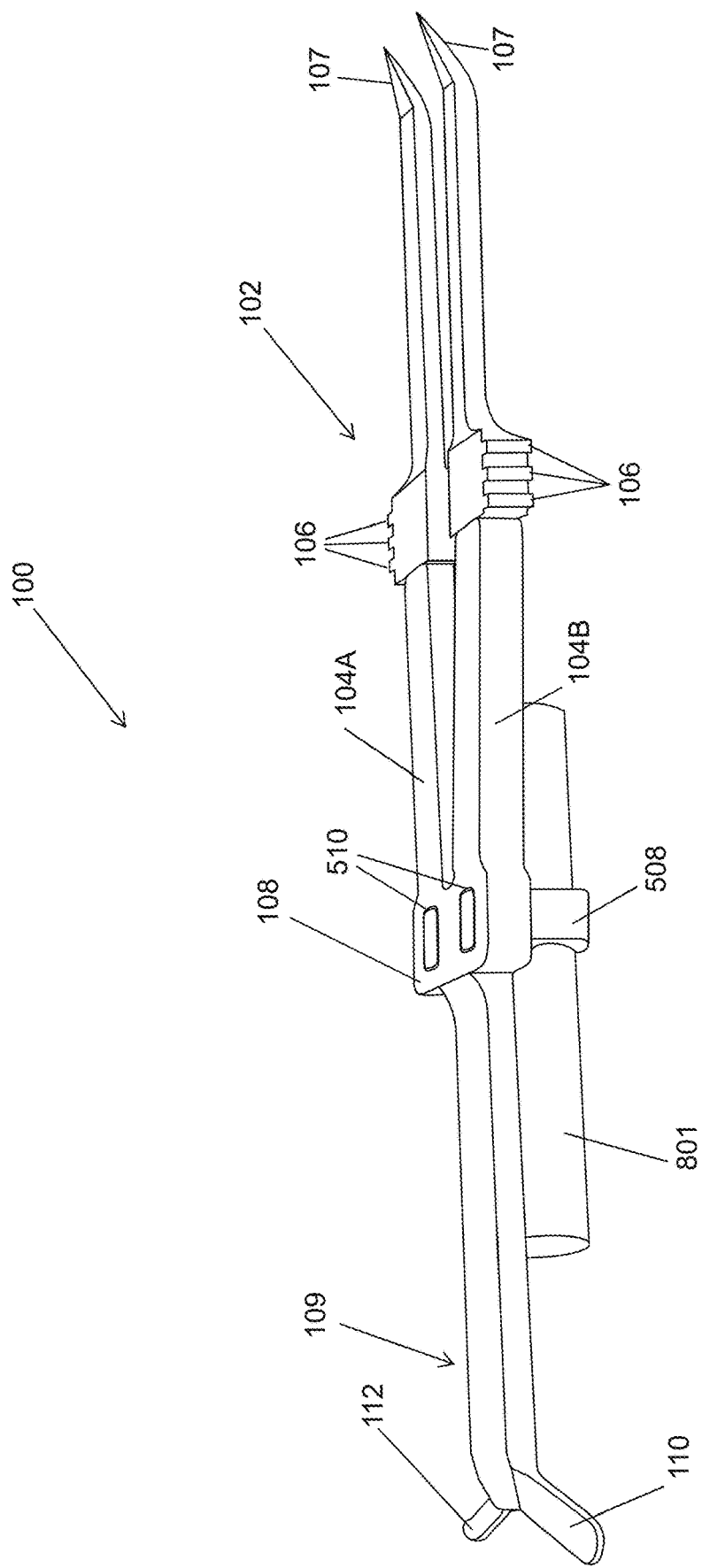

For example, in FIG. 8A, a penlight 801 is inserted into the penlight holder 508, and the penlight holder is secured on a top surface of the dental tool. By contrast, in FIG. 8B, the penlight holder is secured to a bottom surface of the dental tool, and so the penlight 801 is also positioned at the bottom surface.

Figure 9:
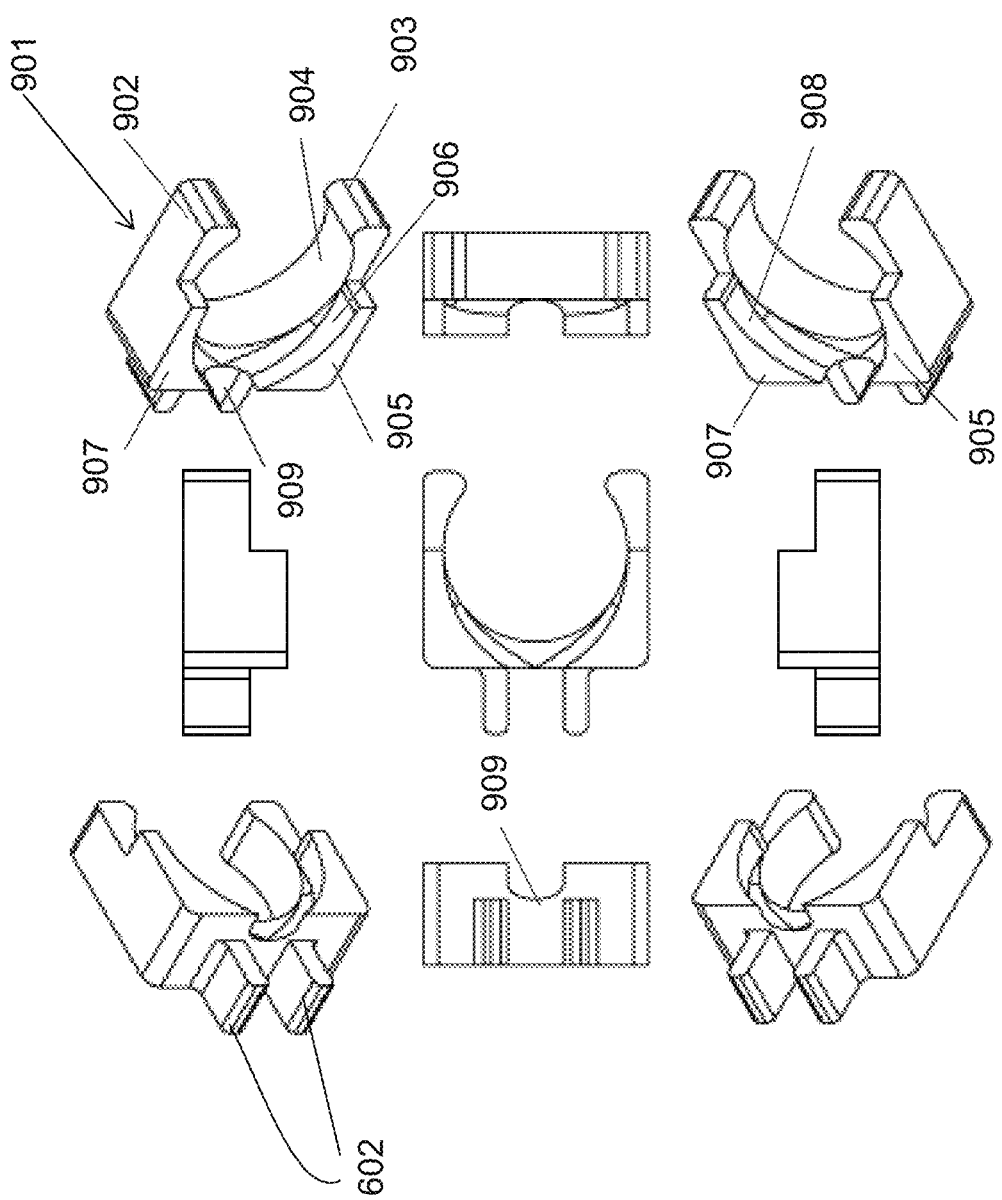
FIG. 9 shows various views of an example embodiment of a removable penlight holder in isolation.

Turning to FIG. 9, various view of another embodiment of a penlight holder 901 are provided. It includes features that are adapted to a specific penlight, which includes a pressable clip to turn on and turn off the penlight.

The holder 901 includes two prongs 902 and 903 that define a connected surface 904 for holding the penlight. The holder also includes protruding structures 907 and 905 that protrude from the same side surface of the prongs 902 and 903. Each of these protruding structures 905 and 907 respectively provide ledges or shoulder surfaces 906 and 908. The shoulder surface 906 at a first end is initially distanced below the connected surface and then curves upwards at a second end to meet the connected surface 904. The shoulder surface 908 at a first end is initially distanced below the connected surface and then curves upwards at a second end to meet the connected surface 904. The first ends of each of the shoulder surfaces 906 and 808 define there between a gap 909.

Turning to FIG. 10A, a side view shows a specific type of penlight 1001 that is inserted into the holder 901. The penlight 1001 has a body 1002 with a clip that protrudes from the body. The clip is used to clip the penlight to a person's shirt or a clipboard. The clip includes a metal arm 1003 that is able to conduct electricity. The end of the arm includes a clip head 1004. When the clip head 1004 is pressed towards the body 1002, the clip head passes through an opening 1006 in the body 1002 and makes physical contact with an electric contact surface 1005, which completes an electric circuit to turn on the light. Upon removing the pressing force, the clip head loses contact with the electric contact surface 1005, and the light turns off.

In a rest position, the clip is oriented in the holder 901 so that the clip head 1004 rests in the gap 909. In this position, the clip head is not in contact with the electric contact surface, and the light remains off.

However, a rotation movement A of the penlight along the penlight's major axis causes the shoulder surface 906 of the protruding structure 905 to press the clip head 1004 against the electronic contact surface, as shown by the resulting movement B in FIG. 10B. As a result, the rotation of the penlight in the pen holder 901 turns on the penlight. A rotation in the reverse direction will turn off the penlight.

Below are example general embodiments and example aspects of a multi-functional dental tool.

In an example embodiment of a dental tool, the dental tool includes: a forcep portion at a first end; a burnisher tool on a second end opposite to the first end; the forcep portion comprising a pair of forcep legs and a joint between the forcep legs; and an elongate body of the burnisher tool extends from the joint.

In an example aspect, the forcep includes grooved grips on the outward face of each forcep leg.

In another example aspect, an end portion of each of the forcep legs has an end portion that is removably attachable from the rest of the dental tool, wherein each of the end portions includes a forcep tip.

In another example aspect, each of the end portions comprises further includes a grip when the end portions are assembled with the dental tool.

In another example aspect, the dental tool further includes a penlight holder positioned at the joint of the dental tool.

In another example aspect, the penlight holder is removably attachable from the dental tool.

In another example aspect, the burnisher tool includes two burnishing ends arranged in a Y-configuration or a T-configuration.

In another example aspect, the burnisher tool includes one burnishing end.

In another example aspect, the penlight holder includes two prongs that define a contact surface to resiliently hold a penlight, and a protruding surface that defines a curved shoulder surface, wherein a first end of the curved shoulder surface is distanced below the contact surface and a second end of the curved shoulder surface meets the contact surface.

In an example embodiment of a kit of parts for a dental tool, the kit of parts includes: a dental tool body including a forcep portion at a first end, a burnisher tool on a second end opposite to the first end; the forcep portion including a pair of forcep legs and a joint between the forcep legs, and an elongate body of the burnisher tool extends from the joint; and a pair of end portions corresponding to the pair of forcep legs, each of the end portions including a forcep tip, and each of the end portions are removably attachable to the each of the forcep legs.

In an example aspect, the kits of parts further includes a removably attachable penlight holder, the penlight holder comprising an attacher to attach to the joint of the dental tool.

In an example embodiment of a kit of parts for a dental tool, the kit of parts includes: a dental tool body including a forcep portion at a first end, a burnisher tool on a second end opposite to the first end; the forcep portion including a pair of forcep legs and a joint between the forcep legs, and an elongate body of the burnisher tool extends from the joint; and a removably attachable penlight holder, the penlight holder including an attacher to attach to the joint of the dental tool.

In an example embodiment of a kit of parts for a dental tool, the kit of parts includes: a dental tool body including a forcep portion at a first end, a burnisher tool on a second end opposite to the first end; the forcep portion including a pair of forcep legs and a joint between the forcep legs, and an elongate body of the burnisher tool extends from the joint; the dental body further including a penlight holder positioned at the joint; and a penlight configured to be removably positioned in the penlight holder.

It will be appreciated that different features of the example embodiments of the dental tool, as described herein, may be combined with each other in different ways. In other words, components, shapes, and configurations may be used together according to other example embodiments, although not specifically stated.

The features described herein are just for example. There may be many variations to these features without departing from the spirit of the invention or inventions. For instance, the features may be added, deleted, or modified.

Although the above has been described with reference to certain specific embodiments, various modifications thereof will be apparent to those skilled in the art without departing from the scope of the claims appended hereto.

The invention claimed is:

1. A dental tool, the dental tool comprising:
   a forcep portion at a first end, the forcep portion comprising a pair of forcep legs and a joint between the forcep legs;
   a burnisher tool on a second end opposite to the first end, wherein an elongate body of the burnisher tool extends from the joint;
   a penlight holder positioned at the joint, wherein the penlight holder includes a first set of prongs that define a contact surface to resiliently hold a penlight, a second set of prongs to attach to the joint of the dental tool, and a protruding surface that defines a curved shoulder surface to interact with the penlight to turn the penlight on or off when the penlight is rotated in the penlight holder; and
   the joint comprising:
      a top surface;
      a bottom surface;
      a set of holes on the top and bottom surfaces for receiving the second set of prongs of the penlight holder.

2. The dental tool of claim 1 in which the forcep portion comprises grooved grips on an outward face of each forcep leg.

3. The dental tool of claim 1 in which a first end portion of each of the forcep legs has a second end portion that is removably attachable from the first end portion, wherein each of the second end portions comprises a forcep tip.

4. The dental tool of claim 3 wherein each of the second end portions further comprises a grip.

5. The dental tool of claim 1, wherein the penlight holder is removably attachable from the dental tool.

6. The dental tool of claim 1 wherein the burnisher tool comprises two burnishing ends arranged in a Y-configuration or a T-configuration.

7. The dental tool of claim 1 wherein the burnisher tool comprises one burnishing end.

8. The dental tool of claim 1 wherein a first end of the curved shoulder surface is distanced below the contact surface and a second end of the curved shoulder surface meets the contact surface.

9. The dental tool of claim 1, wherein the curved shoulder surface is configured to interact with a clip head on the penlight.

10. A kit of parts for a dental tool comprising:
- a dental tool body comprising a forcep portion at a first end, a burnisher tool on a second end opposite to the first end, the forcep portion comprising a pair of forcep legs and a joint between the forcep legs, and an elongate body of the burnisher tool extends from the joint;
- a pair of end portions corresponding to the pair of forcep legs, each of the end portions comprising a forcep tip, and each of the end portions removably attachable to the each of the forcep legs; and
- a penlight holder removably attachable at the joint, wherein the penlight holder includes a first set of prongs that define a contact surface to resiliently hold a penlight, a second set of prongs to attach to the joint of the dental tool, and a protruding surface that defines a curved shoulder surface to interact with the penlight to turn the penlight on or off when the penlight is rotated in the penlight holder;
- the joint comprising:
  - a top surface;
  - a bottom surface;
  - a set of holes on the top and bottom surfaces for receiving the second set of prongs of the penlight holder.

11. The kit of parts of claim 10 wherein a first end of the curved shoulder surface is distanced below the contact surface and a second end of the curved shoulder surface meets the contact surface.

12. The kit of parts of claim 10, further comprising:
the penlight configured to be removably positioned in the penlight holder.

13. The kit of parts of claim 10, wherein the curved shoulder surface is configured to interact with a clip head on the penlight.

* * * * *